United States Patent [19]

Rosa et al.

[11] Patent Number: 4,642,306
[45] Date of Patent: Feb. 10, 1987

[54] CYCLIC DITHIODIACETAMIDES AND COMPOSITIONS CONTAINING THEM

[75] Inventors: Jean Rosa; Jèan-Paul Castaigne, both of Paris; Henri Demarne, Montpellier; Pierre Tozzolino, Morlaas, all of France

[73] Assignees: Sanofi; Institut National de la Sante et de la Recherche Medicale, both of Paris, France

[21] Appl. No.: 611,516

[22] Filed: May 17, 1984

[30] Foreign Application Priority Data

May 17, 1983 [FR] France ................................. 83 08155

[51] Int. Cl.⁴ .................. A61K 31/535; A61K 31/54; C07D 265/30; C07D 279/12
[52] U.S. Cl. .................................... 514/222; 514/228; 514/255; 514/316; 514/422; 544/58.4; 544/85; 546/189; 548/523
[58] Field of Search ...................... 544/58.4, 85, 357; 546/189; 548/523; 514/222, 228, 255, 316, 422

[56] References Cited

PUBLICATIONS

Nishimura et al, Chemical Abstracts, vol. 62, (1965) 2750c.

Primary Examiner—Richard L. Raymond
Attorney, Agent, or Firm—Bacon & Thomas

[57] ABSTRACT

The present invention relates to cyclic dithiodiacetamides with action inhibiting the malformation or the destruction of the red blood corpuscles due to a genetic modification of the haemoglobin or to parasites, of formula:

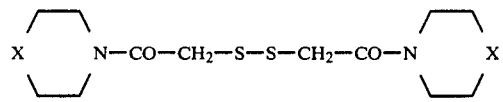

in which X is a direct bond, an atom of oxygen or of sulfur, a methylene group, an ethylene group or an N—R group, where R is an atom of hydrogen or a lower alkyl group, lower (hydroxy)alkyl group, lower alkanoyl group or a phenyl group; to their possible pharmaceutically acceptable salts; to a process for preparing them from a dithiodiacetate or a mercaptoacetate of lower alkyl by transamination and possible oxidation; and to pharmaceutical compositions containing them as active ingredients, useful for the treatment for example of drepanocytosis, or sickle cell anaemia, of malaria and of babebiosis.

7 Claims, No Drawings

CYCLIC DITHIODIACETAMIDES AND COMPOSITIONS CONTAINING THEM

The present invention relates to cyclic dithiodiacetamides, to a process for preparing them and to pharmaceutical compositions for the inhibition of the malformation or destruction of the red blood corpuscles due to a genetic modification of the haemoglobin or to parasites, and therefore useful in the treatment of drepanocytosis, or sickle cell anaemia, and of malaria.

Drepanocytosis is known to be a genetic disease which comprises an abnormality in the structure of the haemoglobin, of which the Glu-6 amino acid of the beta chain is replaced by Val amino acid, giving haemoglobin-S which polymerizes.

This polymerization, during deoxygenation of the red cell, brings about sickling of the latter which becomes rigid, circulates poorly and is blocked in the small vessels. Individuals carrying two sickle cell genes are thus under the permanent threat of a fatal complication.

Certain disulfides have been described in prior literature as inhibiting sickling; in particular, cystamine has been indicated as being particularly active ("Developments of Therapeutic Agents for Sickle Cell Disease", Inserm Symposium, 1979, North Holland: Amsterdam, Editors J. Rosa, Y. Beuzard, J. Hercules; pages 139-153).

It has now been found that the cyclic dithiodiacetamides of formula I:

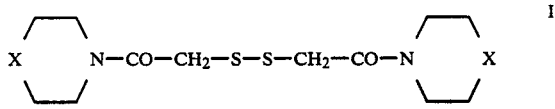

in which X represents a direct bond, an atom of oxygen or of sulfur, a methylene group, an ethylene group or an N—R group, where R is an atom of hydrogen or a lower alkyl group, lower(hydroxy)alkyl group, lower alkanoyl group of a phenyl group, are very active in the inhibition of polymerization of the haemoglobin-S and of the sickling of the red cells.

It has also been surprizingly found that the cyclic dithiodiacetamides of formula I hereinabove are active on the parasites affecting the red blood corpuscles, such as the Plasmodia and the Babesiae. More particularly, they show a schizonticide activity in vitro on "Plasmodium falciparum" and in vivo on "Plasmodium berghei".

The expression "inhibition of the malformation or of the destruction of the red blood corpuscles" as used in the present specification defines an inhibition which may be either direct on the haemoglobin or indirect by inhibition of the growth of the parasites in the red cell.

The present invention thus has for one of its objects the cyclic dithiodiacetamides of formula I hereinabove, as well as their pharmaceutically acceptable salts.

The term "lower alkyl" as used in the present specification denotes the methyl, ethyl, propyl and isopropyl groups.

The term "lower alkanoyl" denotes the formyl, acetyl and propionyl groups.

The present invention has for a further object a process for preparing the cyclic dithiodiacetamides of formula I hereinabove, characterized in that a dithiodiacetate or a mercaptoacetate of lower alkyl, methyl or ethyl, by preference, is treated with a cyclic secondary amine of formula:

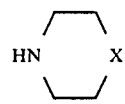

in which X is as defined hereinabove, at a temperature of 15° to 60° C. and, when a mercaptoacetate of lower alkyl is used as starting product, the product thus obtained is subjected to oxydation; and the product thus obtained is possibly converted into its pharmaceutically acceptable salts.

Transamination with amine II may be effected by mixing the reagents without using solvents, or in a solvent, preferably an alcohol, more particularly the same alcohol esterifying the dithiodiacetic acid in the starting product.

After a period of 6 to 24 hours, depending on the temperature, the final product is isolated in accordance with conventional techniques, for example by evaporation and purification.

When a mercaptoacetate of lower alkyl is used as starting product, the product thus obtained, of formula:

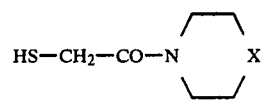

in which X is as defined hereinabove, is subjected to oxydation by leaving it to oxidize in air, possibly enriched with oxygen, in an aqueous solution or in the absence of solvents, or by using an oxidizing agent such as bromine, iodine or hydrogen peroxide.

According to a preferred modus operandi, a 15% hydrogen peroxide solution is used at the temperature of 10°-30° C. The dithiodiacetamide which forms precipitates and is isolated by simple filtration or it is isolated by evaporation, preferably at reduced pressure, of the water.

The cyclic dithiodiacetamides of the present invention present a remarkable biological activity as they prevent the malformation or the destruction of the red blood corpuscles due to drepanocytosis or to parasites, such as the Plasmodia and the Babesiae. More particularly, the cyclic dithiodiacetamides of formula I hereinabove inhibit sickling of the red blood corpuscles in persons suffering from drepanocytosis.

Inhibition of the sickling of human red blood corpuscles has been assessed in accordance with the method consisting in washing and incubating, in a saline buffer (pH 7.40-0.15M), the red cells of the sufferers of the disease for one hour at 37° C. in a water-bath with circular stirring in the presence of the above product at different concentrations. In this operation, the product/haemoglobin molar ratio is tested initially in the interval ranging from 0.5 to 20. As a function of the results obtained, this ratio is modified. At the end of incubation, the excess product is removed by washing. The cellular suspension adjusted to a haematocrit of 5% is transferred into an Erlenmeyer flask and incubated at 37° C. under a stream of a humidified mixture of nitrogen and oxygen. The concentration of oxygen is adjusted by a gas proportioning pump. The effluent gas is transferred into another tube containing formaldehyde. At the end of incubation, the cellular suspension is transferred in the formaldehyde simply by turning the flask over.

The proportion of deformed cells and those having the characteristics of drepanocytes (having filiform extensions) is assessed with the aid of a microscope having a NOMARSKY interferential optical system. Inhibition of sickling was calculated according to the following formula:

$$\frac{\%\ \text{cells in sickle form controls} - \%\ \text{cells in sickle form in the presence of the drug}}{\%\ \text{cells in sickle form of the control}}$$

In this test, a compound representative of the present invention, 4,4-dithiodiacetyldimorpholine (formula I, X=0), showed an inhibition of 75% of sickling.

Under the same conditions, cystamine presented an inhibition of 33%.

The compounds of the present invention are non-toxic and may be used as drugs.

The present invention therefore also relates to pharmaceutical compositions for the inhibition of the malformation or the destruction of the red blood corpuscles due to a genetic modification of the haemoglobin or to parasites, containing, as active ingredients, cyclic dithiodiacetamides of formula I hereinabove, as well as to their possible pharmaceutically acceptable addition salts.

In the pharmaceutical compositions of the present invention for oral, sublingual, subcutaneous, intramuscular, intravenous, transdermic or rectal administration, the active ingredients of formula I hereinabove may be administered in unitary forms of administration, mixed with conventional pharmaceutical supports, i.e., pharmaceutically acceptable carriers to animals and to human beings for the treatment of drepanocytosis, malaria or babebiosis. Among the appropriate unitary forms of administration, there are the forms by the oral route, such as tablets, capsules, powders, granules and oral solutions or suspensions and the forms of sublingual and oral administration, as well as the forms of subcutaneous, intramuscular or intravenous, possibly by perfusion, and rectal administration.

In order to obtain the desired effect, the dose of active ingredient may vary between 0.1 and 100 mg per kg of body weight and per day.

Each unitary dose may contain from 10 to 1000 mg of active ingredient in combination with a pharmaceutical support. This unitary dose may be administered 1 to 4 times per day, possibly by perfusion, for the treatment for example of drepanocytosis, malaria and babebiosis.

Powders for oral administration are prepared simply by crushing the active compound to a suitable fineness and by mixing with a similarly crushed diluent. The diluent may be a material based on edible glucide, such as starch. A sweetening agent or a sugar, as well as a flavoring oil are advantageously present.

The granules intended for reconstitution of a liquid preparation for oral administration are prepared by using water-soluble diluents; the active compound and a water-soluble diluent such as saccharose, glucose, etc . . . are wetted with a binding agent such as acacia mucilage, a solution of gelatin, a solution of methylcellulose, and the product is passed through a sieve by force in order to form granules which are dried. It is advantageous to introduce into the composition a suspension agent such as gum tragacanth.

The capsules are made by preparing a pulverulent mixture as described hereinabove and by placing it in shaped gelatin capsules. As additive to the filling operation, it is advantageous to add a lubricant such as talc, magnesium stearate and calcium stearate to the pulverulent mixture before the filling operation.

Tablets are made by preparing a pulverulent mixture, by granulating or cutting up, adding a lubricant and compressing to form tablets. The pulverulent mixture is prepared by mixing the desired compound, suitably crushed, with a diluent or a base such as starch, saccharose, kaolin, dicalcium phosphate, etc . . . . The pulverulent mixture may be granulated by wetting with a binding agent such as syrup, starch paste or acacia mucilage and by forcing it through a sieve. A method other than granulation may consist in cutting up the pulverulent mixture, i.e. passing it through the tablet-making machine and breaking the resulting tablets which are imperfectly formed into fragments (portions). The portions may be lubricated in order to prevent them from sticking to the tablets and forming cubes, by adding a stearate salt, talc or a mineral oil. The lubricating mixture is then compressed to form tablets.

The tablets may advantageously be provided with a protecting coating constituted by a coat of gum lac, a coat of sugar and methylcellulose, and a coat of varnish of carnauba wax, or they may be treated in another manner so that they have a prolonged or delayed activity and that they continually release a predetermined quantity of active ingredient.

Fluids for oral administration are prepared in unitary dosage forms such as syrups, where every coffee spoonful of composition contains a predetermined quantity of the active compound to be administered.

A preparation in the form of a syrup or elixir may contain the active ingredient together with a sweetening agent, Methylparaben and Propylparaben as antiseptics, as well as a flavouring agent and an appropriate colouring agent.

For rectal application, suppositories are employed which are prepared with binding agents melting at rectal temperature, for example cocoa butter or polyethyleneglycols.

For parenteral application, injectable sterile solutions, aqueous suspensions or isotonic saline solutions are used which contain pharmaceutically compatible dispersion and/or wetting agents, for example propyleneglycol or butyleneglycol.

The active ingredient may also be formulated in the form of microcapsules, possibly with one or more supports or additives.

The following Examples illustrate the invention without, however, limiting it.

EXAMPLE 1

A. 0.1 mole of methyl thioglycolate is introduced into an Erlenmeyer flask provided with a magnetic stirrer, then 0.11 mole of pyrrolidine is added and stirring is maintained for 6-12 hours at ambient temperature. At the end of reaction, the excess pyrrolidine is eliminated and the product obtained is subjected to a fractional distillation under reduced pressure. 1-mercaptoacetylpyrrolidine is thus obtained with a yield of 86% after distillation.

By operating as described hereinabove, but replacing the pyrrolidine by 0.11 mole of 1-methylpiperazine and of morpholine, the following are respectively obtained:
- 1-methyl-4-mercaptoacetylpiperazine and
- 4-mercaptoacetylmorpholine B. 0.1 mole of 1-mercaptoacetylpyrrolidine is introduced into an Erlenmeyer flask provided with a magnetic stirrer. 0.1 mole of 15% hydrogen peroxide is added, maintaining the temperature of the medium between 10° and 15° C. and the medium is then stirred for 2 hours at ambient temperature. By cooling in an ice bath, the crystals of disulfide appear. The product is filtered, dried and possibly recrystallized in water or in a water/ethanol mixture. With a yield of 90%, 1,1'-dithiodiacetyldipyrrolidine is thus obtained (formula I, X=direct bond); m.p. 79° C. (Kofler).

By operating as described hereinabove, from 1-methyl-4-mercaptoacetylpiperazine and from 4-mercaptoacetylmorpholine, the following are respectively obtained:
- 4,4'-dithiodiacetyldi-(1-methyl)piperazine (formula I, X=N—CH$_3$); m.p. 110° C. (Kofler); and
- 4,4'-dithiodiacetyldimorpholine (formula I, X=oxygen), in the form of viscous liquid.

EXAMPLE 2

To a solution of 47.6 g of ethyl dithiodiacetate in 150 ml of ethanol are added 34.8 g of morpholine. The mixture thus obtained is heated to 50° C. for 24 hours, then the ethanol and the excess morpholine are evaporated under reduced pressure. 4,4-dithiodiacetyldimorpholine is thus obtained in the form of viscous liquid.

In the same way, by treating 0.2 mol of ethyl dithiodiacetate with, respectively, 0.4 mole of pyrrolidine and 0.4 mole of 1-methylpiperazine in ethanol, the following are respectively obtained:
- 1,1'-dithiodiacetyldipyrrolidine; m.p. 79° C. (Kofler) and
- 4,4'-dithiodiacetyldi-(1-methyl)piperazine; m.p. 110° C. (Kofler).

EXAMPLE 3

A composition for tablets is prepared containing, as active ingredient, one of the compounds described in Examples 1 and 2, having the

| active ingredient | 500 mg |
| --- | --- |
| glycine | 120 mg |
| microgranular cellulose | 70 mg |
| precipitated silica | 18 mg |
| carboxymethyl starch | 30 mg |
| magnesium stearate | 11 mg |
| talc | 11 mg |

The calculated quantities of the components are mixed for 30 minutes, then the mixture is granulated dry and passed through a sieve with 1.6 mm mesh. It is then compressed, using a punch in the form of a small rod. In this way, tablets are obtained, each weighing 760 mg and each containing 500 mg of active ingredient.

EXAMPLE 4

Tablets are prepared according to Example 3. The tablets thus obtained are coated with the aid of a suspension of dibutyl phthalate, butyl polymethacrylate and dimethylaminoethyl, polyethyleneglycol 1500, precipitated silica, titanium dioxide and talc in a 1:1 acetone/isopropanol mixture having a concentration of dry residue of about 10%. Coated tablets are thus obtained, each weighing 780 mg and each containing 500 mg of active ingredient.

EXAMPLE 5

A granule is prepared, intended for reconstitution of an oral liquid preparation, containing, as active ingredient, one of the compounds described in Examples 1 and 2, having the following composition:

| active ingredient | 3.60 g |
| --- | --- |
| saccharose | 50.00 g |
| sodium carboxymethylcellulose | 0.80 g |
| citric acid | 0.10 g |
| trisodium citrate | 0.90 g |
| sodium benzoate | 0.25 g |
| sodium saccharine | 0.15 g |
| aromatizing agent | 0.50 g |

The volume of the granule thus obtained is taken to 100 ml with water for syrups. A unitary dose of 5 ml of the extemporaneous syrup thus obtained contains 180 mg of active ingredient.

To prepare the granule, the calculated quantities of all the components, except saccharose, are pulverized, then the powder thus obtained is mixed with the saccharose until a homogeneous granule is obtained.

EXAMPLE 6

A granule intended for reconstitution of an oral liquid preparation is prepared according to Example 5, having the following composition:

| active ingredient | 7.00 g |
| --- | --- |
| saccharose | 46.60 g |
| sodium carboxymethylcellulose | 0.90 g |
| citric acid | 0.10 g |
| trisodium citrate | 0.90 g |
| sodium benzoate | 0.25 g |
| sodium saccharine | 0.15 g |
| aromatizing agent | 0.50 g |

A unitary dose of 5 ml of the extemporaneous syrup thus obtained contains 350 mg of active ingredient.

EXAMPLE 7

A granule intended for reconstitution of an oral liquid preparation is prepared according to Example 5, having the following composition:

| active ingredient | 8.00 g |
| --- | --- |
| saccharose | 45.60 g |
| sodium carboxymethylcellulose | 1.00 g |
| citric acid | 0.10 g |
| trisodium citrate | 0.90 g |
| sodium benzoate | 0.25 g |
| sodium saccharine | 0.15 g |
| aromatizing agent | 0.50 g |

A unitary dose of 5 ml of the extemporaneous syrup thus obtained contains 400 mg of active ingredient.

EXAMPLE 8

Tablets based on one of the compounds described in Examples 1 and 2 are prepared, having the following composition:

| active ingredient | 350 mg |
| --- | --- |

| | |
|---|---|
| microcrystalline cellulose | 100 mg |
| lactose | 125 mg |
| magnesium stearate | 10 mg |
| talc | 15 mg |

The powders are passed through a sieve with 0.3 mm mesh, then the ingredients are mixed until a homogeneous mixture is obtained which is compressed and granulated. The granules thus obtained are used for forming tablets by compression. Weight of a tablet: 600 mg.

EXAMPLE 9

Tablets based on one of the compounds described in Examples 1 and 2 are prepared, having the following composition:

| | |
|---|---|
| active ingredient | 150 mg |
| microcrystalline cellulose | 75 mg |
| talc | 15 mg |
| polyvinylpyrrolidone | 30 mg |
| precipitated silica | 25 mg |
| magnesium stearate | 5 mg |

All the ingredients, except the lubricant, are mixed intimately in a mixing-kneading machine for 15 minutes, then the mixture is kneaded with gradual addition of water. The mass is passed through a sieve with 1.25 mm mesh. The granule is dried in an oven with forced ventilation until a relatively reduced residual humidity is obtained (about 2%). The granule is rendered uniform, the lubricant is added and tablets are formed by compression. Weight of a tablet: 300 mg.

Tablets containing 250 mg of active ingredient are prepared in the same manner.

EXAMPLE 10

Coated tablets based on one of the components described in Examples 1 and 2, having the following composition:

| | |
|---|---|
| active ingredient | 150 mg |
| carboxymethyl starch | 10 mg |
| microcrystalline cellulose | 85 mg |
| lactose | 135 mg |
| hydrogenated castor oil | 10 mg |
| magnesium stearate | 5 mg |
| are prepared by operating as described in Example 9. The tablets thus obtained are coated with a coat having the following composition: | |
| butyl phthalate | 0.300 mg |
| butyl polymetacrylate and dimethylaminoethyl | 1.850 mg |
| polyethyleneglycol 1500 | 0.080 mg |
| precipitated silica | 0.020 mg |
| talc | 0.900 mg |
| titanium dioxide | 1.850 mg | dissolved in a solvent which is eliminated by evaporation in an oven with forced ventilation. Weight of a tablet: 400 mg.

EXAMPLE 11

Suppositories based on one of the compounds described in Examples 1 and 2 are prepared, having the following composition:

| | |
|---|---|
| active ingredient | 300 mg |
| mass for suppositories | 1450 mg |

The finely pulverized active substance is suspended in the mass for suppositories at 37° C. and the mixture is poured into moulds slightly cooled beforehand. Weight of a suppository: 1750 mg.

What is claimed is:

1. Cyclic dithiodiacetamide of formula:

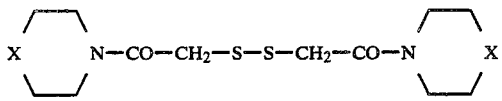

in which X represents a direct bond, an atom of oxygen or of sulfur, a methylene group, an ethylene group or an N—R group, where R is an atom of hydrogen or a lower alkyl group, lower (hydroxy)alkyl group, lower alkanoyl group or a phenyl group, and the pharmaceutically acceptable salts thereof.

2. 4,4'-dithiodiacetyldimorpholine.
3. 1,1'-dithiodiacetyldipyrrolidine.
4. 4,4'-dithiodiacetyldi-(1-methyl)piperazine.
5. A pharmaceutical composition for inhibition of malformation or the destruction of the red blood corpuscles due to a genetic modification of haemoglobin or to parasites, which comprises, as active ingredient, an effective amount for inhibition of malformation of the destruction of the red blood corpuscles due to genetic modification of haemoglobin or to parasites of a compound of claim 1 and a pharmaceutically acceptable carrier.
6. Pharmaceutical composition of claim 5, which is in the form of dosage unit.
7. Pharmaceutical composition of claim 6 wherein each dosage unit contains 10 to 1000 mg of active ingredient.

* * * * *